United States Patent
Guarnieri

(10) Patent No.: US 8,206,440 B2
(45) Date of Patent: Jun. 26, 2012

(54) IMPLANTABLE OCULAR MICROAPPARATUS TO AMELIORATE GLAUCOMA OR AN OCULAR OVERPRESSURE CAUSING DISEASE

(75) Inventor: Fabio Ariel Guarnieri, Paraná (AR)

(73) Assignees: Consejo Nacional De Investigaciones Cientificas Y Technicas, Buenos Aires (AR); INIS Biotech LLC, Milford, DE (US)

( * ) Notice: Subject to any disclaimer, the term of this patent is extended or adjusted under 35 U.S.C. 154(b) by 348 days.

(21) Appl. No.: 12/522,320

(22) PCT Filed: Dec. 17, 2007

(86) PCT No.: PCT/IB2007/055169
§ 371 (c)(1),
(2), (4) Date: Jul. 29, 2009

(87) PCT Pub. No.: WO2008/084350
PCT Pub. Date: Jul. 17, 2008

(65) Prior Publication Data
US 2010/0042209 A1    Feb. 18, 2010

(30) Foreign Application Priority Data
Jan. 8, 2007    (AR) .............. P20070100073

(51) Int. Cl.
*A61F 2/14*    (2006.01)
*A61M 5/00*    (2006.01)
(52) U.S. Cl. ................ 623/4.1; 604/8; 604/9
(58) Field of Classification Search .......... None
See application file for complete search history.

(56) References Cited

U.S. PATENT DOCUMENTS

| | | | | |
|---|---|---|---|---|
| 6,475,639 B2 * | 11/2002 | Shahinpoor et al. | ......... | 428/614 |
| 6,579,235 B1 * | 6/2003 | Abita et al. | .................... | 600/398 |
| 6,589,198 B1 * | 7/2003 | Soltanpour et al. | ............... | 604/9 |
| 6,682,500 B2 * | 1/2004 | Soltanpour et al. | ............... | 604/9 |
| 6,976,998 B2 * | 12/2005 | Rizzo et al. | .................. | 623/6.63 |
| 2003/0139808 A1 * | 7/2003 | Shahinpoor et al. | ........... | 623/4.1 |
| 2003/0214199 A1 * | 11/2003 | Heim et al. | .................... | 310/309 |
| 2005/0049578 A1 | 3/2005 | Tu et al. | | |

FOREIGN PATENT DOCUMENTS

DE            44 38 201            5/1996
(Continued)

OTHER PUBLICATIONS

International Search Report, PCT/IB2007/055169, Aug. 4, 2008.
Po-Jui Chen et al:, "Implantable micromechanical parylene-based pressure sensors for unpowered intraocular pressure sensing; Implantable micromechanical parylene-based pressure sensors", Journal of Micromechanics & Microengineering, Institute of Physics Publishing, Bristol, GB, vol. 17, No. 10, Oct. 1, 2007, pp. 1931-1938, XP020119928, ISSN: 0960-1317.

*Primary Examiner* — David H Willse
*Assistant Examiner* — Javier Blanco
(74) *Attorney, Agent, or Firm* — Young & Thompson

(57) ABSTRACT

A microapparatus (11) implantable in the eye (13) includes a cuasi-bistable microvalve (21) commanded by an intraocular pressure sensor (23) in situ. The microvalve mechanism includes a diaphragm (27) made of a conjugated polymer (29) that shows high deformation and biocompatibility capabilities and which volume depends from the electric potential applied by its pair of electrodes (31). The sensor and actuator-valve are coupled to a drainage conduit (15), the first to deform by the pressure in the ocular globe and the second in a position of buckling to normally close the drainage conduit. The sensor has a membrane of conductive polymeric material with these same properties and whose ohmic resistance varies with the mechanical deformation produced by the ocular pressure.

14 Claims, 3 Drawing Sheets

FOREIGN PATENT DOCUMENTS

| | | | | | |
|---|---|---|---|---|---|
| DE | 100 41 085 | 3/2002 | WO | WO 90/13750 | 11/1990 |
| EP | 1 184 010 | 3/2002 | WO | WO 99/38470 | 8/1999 |

* cited by examiner

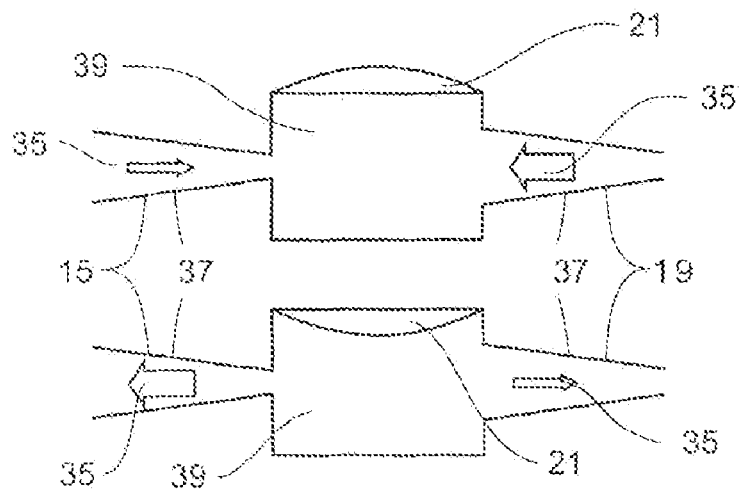
Fig. 4A
Fig. 4B
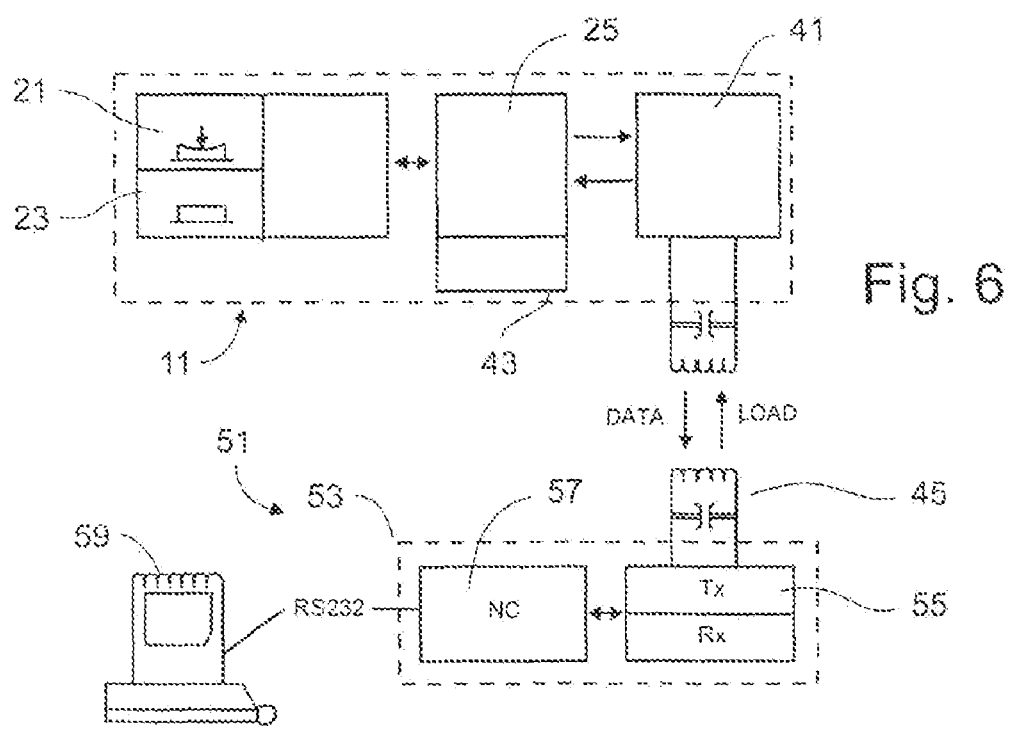
Fig. 6

IMPLANTABLE OCULAR MICROAPPARATUS TO AMELIORATE GLAUCOMA OR AN OCULAR OVERPRESSURE CAUSING DISEASE

TECHNICAL FIELD

This invention is applicable to opthalmologic surgery and refers to amelioration or eventual cure of high intraocular pressure related to glaucoma.

Glaucoma is a general term for a progressive disease that leads to blindness caused by a gradual, sometimes rapid, increase of the intraocular pressure. This pressure increase is considered a very important risk factor. It is estimated that about 67 million people suffers from this disease in the world.

BACKGROUND ART

There are drug and surgical treatments to decrease intraocular pressure. When therapy and surgery do not work, implants are used (in the form of bypasses known in the field as 'shunts') with passive valves that drain the intraocular liquid (aqueous humor) to the outside through tubes and plates. See, for example, Lim, K. S., 'Glaucoma drainage devices, past, present and future', Br. J. Ophtalmol (1968), 82:1083-1089 or the international patent (PCT) WO99/66871, which describes a device—of about 1 mm long—implantable in the eye to decrease ocular pressure by a stopper that regulates pressure, that releases when an optimal value is exceeded to drain the liquid that is absorbed by the surrounding tissues. However, said implants have shown so far some drawbacks, such as:

- the implant size is not small enough (lower than 1 cm) nor material are adequate to avoid fibrosis (see, Lim et al, *Glaucoma drainage devices; past, present and future*), Br J Ophthalmol 1998; 82:1083-1089)
- Surgery is not able to optimize or turn intraocular pressure predictable, resulting in hypotony or high resistance to flow (see, Q H. Nguyen, '*Avoiding and managing complications of glaucoma drainage implants*', Curr Opin Ophthalmol 15:147-150, 2004)
- Intraocular pressure varies during the day, a variation that can not be compensated by passive valves (see, Kitazawa Y, Horie T. '*Diurnal variation of intraocular pressure in primary open-angle glaucoma*', Am J Ophthalmol, 1975; 79:557-566)
- There is obstruction by particles (proteins or cells) due to hydrophobicity of the silicon used to make the implant. See, '*A Compact Chemical-Resistant Microvalve Array Using Parylene Membrane and Pneumatic Actuation*', Z Hua, O Srivannavit, Y Xia, E Gulari—MEMS, NANO and Smart Systems, 2004. ICMENS 2004. Proceedings . . . , 2004—ieeexplore.ieee.org.

There have been attempts to replace said passive valves by electrochemical or electromagnetic actuating microvalves using MEMS technology. To this respect, reference can be made to the article of Byunghoon B., '*In vitro experiment of the pressure regulating valve for a glaucoma implant*', J. Micromech. Microeng. (2003), 13:613-619, wherein an ocular implant to decrease glaucoma by an electromagnetic valve opening or closing mechanism and a permanent magnet moved by the magnetic force deforming the membrane is shown. The membrane is made of a deformable polymer of low elasticity module (Young module). Also, the U.S. Pat. No. 6,168,575 issued to Soltanpour et al, entitled '*Method and apparatus for controlling intraocular pressure*', describes a small pump of 5 to 15 mm of length which is implanted in the eye to remove the excess of fluid that can be adjusted manually or automatically. Control is made by a pressure sensor connected to a microprocessor, being the sensor disposed externally to the eye. Said US Patent discusses the drawbacks of the automatic adjustment as to the complications related to muscular hypotony.

U.S. Pat. No. 6,589,203 describes an ocular implantable device having a deformable surface made of a material capable of supporting continuous deformations and a drainage tube that has a valve sensible to pressure variations that limits the flow by the tube. Most recent reference is U.S. Pat. No. 6,682,500 issued to Soltanpour et al, entitled 'Synthetic muscle-based diaphragm pump apparatuses' that describes a device with a diaphragm pump made of a synthetic polymer of a metal compound and includes a pressure sensor. This apparatus is equipped with two valves, one in the inlet conduit to the pump and the other in the outlet conduit, to regulate the flow of fluid in the pump. This reference also allows implementing an inductive coupling to transfer signals between the implant and an external accessory.

Unfortunately, the abovementioned implants have biocompatibility and size problems as the previous ones that do not allow meeting design requirements. Problems such as malfunctioning and obstruction have not been addressed by said patents.

Less relevant references but that could be also of interest in the field are the French Patent 2.553.658 (valve implant to cure glaucoma) and the U.S. Pat. Nos. 4,282,882 (apparatus to modify intraocular pressure), 4,402,681 (implantable artificial valve to regulate intraocular pressure), 4,585,457 (inflatable intraocular lens), 4,886,488 (glaucoma lachrymal drainage system and method), 5,041,081 (ocular implant to control glaucoma), 5,127,901 (implant with sub-conjuntival arc), 5,433,701 (apparatus to reduce ocular pressure), 5,454,796 (device and method to control intraocular fluid pressure), 5,520,631; 5,704,907 and 6,102,045 (methods and apparatuses to decrease intraocular pressure), 5,523,808 (ophthalmic apparatus provided with a measuring system of the intraocular pressure), 5,626,559 (ophthalmic device to drain excess intraocular fluid), 5,651,782 (method and apparatus to implant a mesh in glaucoma surgery), 5,656,026 (in vitro assay method of a valve unidirectional gradient limiting device to drain glaucoma), 5,713,844 (device and method to regulate intraocular pressure), 5,743,868 (cornea implantable device to regulate pressure), 5,785,674 (device and method for treating glaucoma), 5,807,302 (treatment of glaucoma), 5,868,697 (intraocular implant), 5,968,058 (device and method to implant an intraocular implant), 6,077,299 (non-invasive implant with adjustable valve to drain aqueous humor in glaucoma), 6,083,161 (apparatus and method for improving establish ocular pressure), 6,113,342 (diagnosis method and apparatus for providing the effective intraocular pressure based in cornea measurements), 6,142,990 (medical apparatus, specially to reduce intraocular pressure), 6,464,724 (stent device and method for treating glaucoma), 6,468,283 (method for regulating pressure with an ocular implant), 6,510,600 (method for manufacturing a flow regulating implant), 6,558,342 and 6,726,664 (flow control devices, introducers, and methods of implanting), 6,638,239 (apparatus and method for treating glaucoma) and 6,730,056 (eye implant for treating glaucoma and method for manufacturing the same).

SUMMARY OF THE INVENTION

In view of abovementioned references, the objects of the present invention are:

miniaturization of the implant using MEMS technology to make the size of the implant small enough, to avoid that micro movements cause reactions of the surrounding tissue (fibrosis) obstructing drainage and to allow adding other functionalities such as actuator/sensor.

Active control of the intraocular pressure and drainage considering variations of the pressure, whether by diurnal cycles, during the implant, dynamics of the disease, etc.

Biocompatibility of the implant during its lifetime by incorporating MEMS processable and reduced or minimum reactive materials such as polyimide and parylene (this is less hydrophobic than conventionally used silicone), as well as low voltage actuating means such as conjugated polymers.

To avoid hypotony and increase of resistance by fibrosis and particle obstruction by an actuator/sensor system with large displacements of the actuator/valve by using low rigidity polymeric materials in order to attain an opening that allows passing proteins and cells, together with the chance of a pumping mode in case of high resistance to flow as in case of advanced glaucoma or obstruction.

Further objects include:

Reliable design that allows a long lifetime of the implant;

Telemetric follow-up allowing to modify the treatment strategy, for example, changing the control intraocular pressure or testing the implant operation; and Minimizing the power consumption of the implant.

The present invention is a microapparatus (or micro implant) implantable in the eye of the type comprising a microvalve controlled by an intraocular pressure sensor in situ. The objects are achieved by implementing the actuator as a microvalve consisting of a diaphragm or membrane or other flow obstructive means made of a polymeric material selected for showing high deformability as well as biocompatibility, and commanding this mechanism from a sensor also comprising a membrane made of a polymeric material which combines these same properties. The sensor and actuator-valve elements are connected to a drainage conduit, the first to deform by the pressure of the ocular globe and the second in a buckling position to normally close the drainage conduit avoiding in case of malfunctioning that the valve stays open and causes hypotony.

The polymeric material of the sensor is conductive so that its ohmic resistance varies with its mechanical deformation to generate a signal indicative of the ocular pressure. The material of the mechanism actuator-valve is a conjugated polymer which volume changes, for example when it is oxidized or reduced by a ionic migration in an electrolyte medium (as the aqueous humor) produced by the voltage between two electrodes. Its compared advantages are as follows:

Big deformations with low voltage (1 volt)
Minimum energy to change from close to open status
Biocompatible (can work in humid environments as the aqueous humor)
Microprocessable
Quick enough to actuate (few seconds)

This material allows an opening of the microvalve big enough to drain particles that may obstruct the device. The power consumption is minimized as it is a cuasi-stable mechanism, a feature shown by this material and not by those disclosed in other patents (the term 'cuasi-stable' as used herein means that practically current is only consumed when switching between its two states as in one state—closed—there is no voltage and no consumption and in the other—open—a constant potential is kept and there could be little consumption of current by losses).

This actuator-valve mechanism deforms, opening the drainage conduit, as soon as it is subjected to flexion by an electrical field that responds to said overpressure signal generated by the sensor when detecting an ocular overpressure related to a determined threshold. The connection between both diaphragms—the sensor and actuator-valve—is some useful circuit that irradiates an electrical field when the pressure signal exceeds the reference threshold, such as an electronic microcontroller.

The use of the microcontroller allows incorporating additional features, such as adjusting externally the overpressure threshold by a telemetric link through which, also, electrical energy is transferred to a power supply that powers the implant. The power supply may be passive, i.e. it is transferred telemetrically to the implant components without own storage, or preferably active, having a cell within the implant telemetrically rechargeable, conveniently by an inductive coupling.

The valve design is such that, in case of failure and absence of electrical voltage, its status is normally closed, as the diaphragm closes the valve to the non-operative status.

DESCRIPTION OF DRAWINGS

These and other features and details of the object of the invention and the way the invention can be developed and practiced shall be better understood by the following detailed description of an exemplary non-limiting embodiment illustrated in the attached drawing. Other variations, modifications, adaptations and/or additions can be made without departing from the spirit and scope of the invention.

FIGS. 4A and 4B are cross-section schematic details of the valve subjected to a pumping action.

FIG. 6 is a block diagram of the inductive telemetric device of FIG. 5.

PREFERRED EMBODIMENT OF THE INVENTION

Figure 1A:
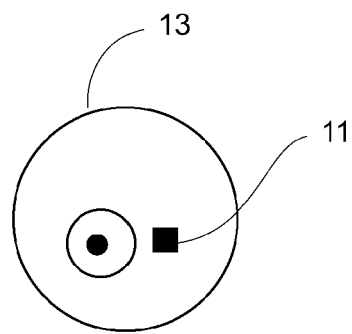
FIG. 1A: Scheme of an eyeball showing, at scale, an implanted microapparatus according to this invention.
Figure 1B:
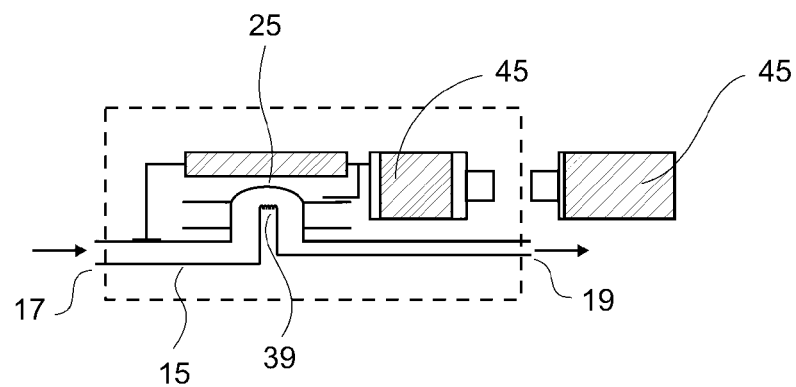
FIG. 1B: Block diagram magnified of the implanted microapparatus, of FIG. 1A.

FIG. 1A shows schematically the different blocks comprising the microapparatus 11 of the present invention, which is surgically implanted to detect and correct glaucoma in an eye and in FIG. 1B the different blocks that conform the microapparatus 11. The microapparatus 11 uses a silicon rubber tube 15 having an inlet end 17 which is implanted in fluid communication with the aqueous humor in the ocular globe 13, more specifically in the sclera, a few millimeters from the corneal limb. The discharge end 19 may be free so that the drained fluid is absorbed by surrounding tissue.

Around the drainage end 19 of conduit 15 there is a valve comprised by a membrane made of dielectric material disposed as a diaphragm 21 that normally (i.e. under normal pressure in the eye 13) closes tube 15. At a middle portion of the drainage tube 15 there is a sensor membrane 23 made of electro conductor material the ohmic resistance of which varies with the deformation the membrane 23 is subjected to by the pressure of liquid inside the tube 15. Microcontroller 25 controls the state of the valve actuator 21 based on the state of sensor 23.

Figure 2:
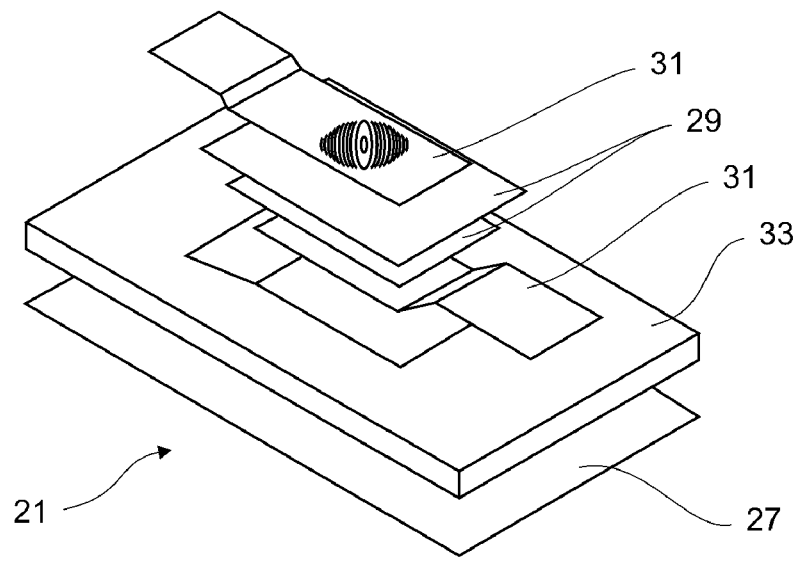
FIG. 2 is a perspective schematic view of the parts of a structure made of membrane for the sensor or the actuator of the implant of FIG. 1.

As shown in FIG. 2, both the pressure sensor 23 and the valve 21 are made using MEMS technology, in a structure comprised by the membrane of biocompatible polymeric material 27 and an electro active polymer 29 between two electrodes 31 made of gold over a silica or Kapton substrate (polyimide, from Dupont) 33, one of which is fixed to the corresponding inner face of the membrane 27. Electrodes may be made of thin layers (micrometric thicknesses) by spin-coating in solvents or thicker layers, of 0.3 to 0.8 mm thick, by dip-coating. There is a wide variety of materials that can be used for the electro active polymer, for example ionic and conjugated materials. For the sensor 23, the conductive polymer 29 can be polypyrrole and, for the actuator 21, the conjugated polymer can be a dual layer 29 of polypyrrole/Nafion (as shown in FIG. 2).

The active device comprised by sensor 23, microcontroller 25 and diaphragm 21, as well as its eventual accessories, are integrated to a chip made by CMOS technology, to which the drainage tube 11 is also integrated by encapsulation techniques with polymer deposition as parylene-c, a material that has been found superior to silicone in terms of biocompatibility, particularly hydrophobicity (resistance to humidity); see Stieglitz T, '*Methods to Determine the Stability of Polymer Encapsulations*', 10$^{th}$ Annual Conference of the International FES Society, July 2005—Montreal, Canada.

The dimensions of the prior art devices, of about 1 cm, produce fibrosis, as previously noted. Since the implant of the invention is 3 mm in its maximum dimension (including the encapsulation), it provides an important feature that cooperates to reduce fibrosis.

Figure 3A:
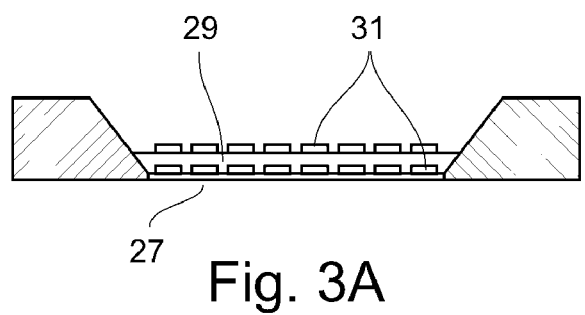
FIGS. 3A and 3B are cross-section schematic views of the structure made of membrane of FIG. 2 shown in the statuses normal closed and open activated, respectively.

The actuator-valve 21 is designed to adopt the normally-closed position in the absence of bias, as shown in FIG. 3A, avoiding hypotony in case of failure. The electrodes 31 of sensor 23 are polarized by a low electrical current so that, in case the fluid pressure inside conduit 15 exceeds the glaucoma threshold, the resistance variation of sensor 23 is detected by the microcontroller 25 that stores a reference value of that threshold. The microcontroller chip 25 may comprise a Wheatstone bridge the imbalance of which is measured by the microcontroller 25 as a signal of pressure.

Figure 3B:
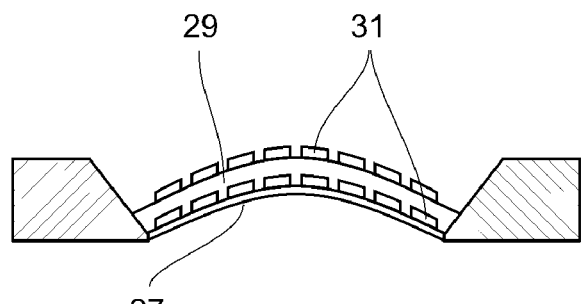

In case pressure exceeds that glaucoma threshold, the microprocessor 25 activates an output that biases the electrodes 31 of microvalve 21, producing an electrical field that deforms the diaphragm 29 of valve 21, displacing the membrane 27 of the actuator-valve structure 21 in the same direction, as shown in FIG. 3B, forcing the opening of conduit 15 to allow drainage of excess fluid. The pressure range of the valve 21 is set from 1 to 4 kPa over the atmospheric pressure, at a very low fluid flow, of about 1 to 3 ml/min.

Preferably, the walls of conduit 15 are angled 37 adjacent to valve 21, in convergent direction at both sides in the flux direction, as schematized by FIGS. 4A and 4B. In this way, in case that flow resistance increases and the opening of the microvalve 21 is not enough due to excessive fibrosis or progression of the disease (advanced glaucoma), microcontroller 25 is able to increase opening and closing cycles causing pumping. Reflux is decreased by the angled 37 inlet and outlet walls that offer an inertial resistance (nozzle/diffuser). Both states of the actuator-diaphragm assembly 21 are observed: volume increase in chamber 39 in FIG. 4A and volume decrease in chamber 39 in FIG. 4B indicating flow rate by the arrows 35. This flow rectification is possible even for low Reynolds numbers as in the case of drainage of intraocular liquid; see Singhal V., '*Numerical Characterization Of Low Reynolds Number Flow Through The Nozzle-Diffuser Element In A Valveless Micropump*' Proc. of 6$^{th}$ ASME/JSME Thermal Engineering Joint Conf, Kohala, 2003.

Figure 5:
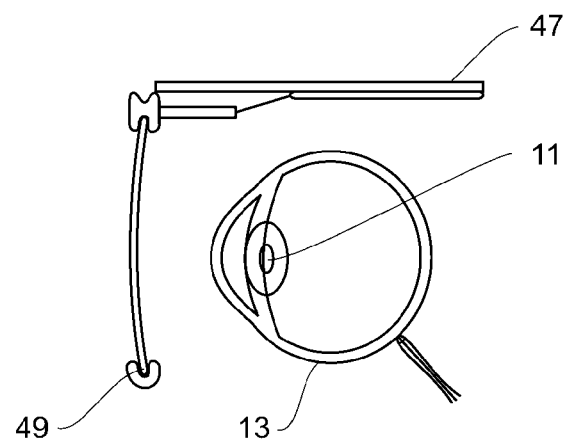
FIG. 5 is a schematic horizontal section view of an eye with and implant of FIG. 1 and a telemetric device to transfer energy and electric energy to the same.

As shown in FIG. 5, the microcontroller 25 is connected to an inductive coupling or antenna 41 to transmit telemetric data related to the implant operation, such as adjusting the pressure threshold. The antenna 41 is also used for the power supply of the microapparatus 11, particularly to bias sensor 23 and the electronic circuit that includes the microcontroller 25 as well as to power the field generator 29 for the microvalve 21.

The power supply can be active, i.e. having a battery 43—for example a Li-ion or LiMn rechargeable microbattery—that is recharged by the inductive coupling 45 or passive, i.e. having no battery, in which case the apparatus is intermittently activated when antenna 41 receives an external charge. The selection of one or the other type of power supply depends on the use, as the microbattery 43 is suitable for permanent continuous uses, while it is not necessary for demand uses, wherein the ophthalmologist can resort to energy transmission. In both cases a charging device with an antenna 45 is provided, which can be located inside the arm 47 or the frame 49 of eyeglasses, as shown in FIG. 4, to couple by proximity with the internal antenna 41. This system has also been implemented in the apparatus of abovementioned U.S. Pat. No. 6,682,500.

FIG. 6 shows the complete mini-system including the implantable microapparatus 11 and an external accessory micro-system 51 coupled by the respective antennas 41 and 45. The component 53 located inside the eyeglass 47-49 is a transponder circuit 55 to transfer load to the internal microapparatus 11 and receive data related to operation of the same, which is used by a microprocessor 57. At the end of the arm 47 of the eyeglasses, there is a RS232 connection to unload data to a PC 59.

Obviously many modifications can be made in the practice of this invention without departing from the scope of the invention. For example, notwithstanding that a piezoresistive sensor 23 has been mentioned, other types of sensors can be used such as capacitive sensors, as well as other materials for the micro-actuator such as carbon nanotubes and compounds with conductive or conjugated polymers, as well as the use of a microbattery 33, however other interesting variations include the use of vibration powered microgenerators, solar cells, body thermal or biochemical energy converters, etc.

The invention claimed is:

1. A glaucoma shunt microapparatus (11) implantable in an eye to ameliorate glaucoma or ocular overpressure causing disease, the microapparatus being made using MEMS technology, said microapparatus comprising:

a drainage conduit (15) having an inlet end (17) implantable in fluid communication with the aqueous humor in the ocular globe (13) of a patient, and an opposite outlet end (19) adapted for draining fluid into the surrounding tissue, an actuator (21) comprising a normally-closed valve arranged in said drainage conduit and including an electrically-deformable actuator diaphragm made of a conductive or other conjugate polymeric material;

a pressure sensor (23) for sensing fluid pressure in said drainage conduit between said inlet end and said valve and opening said valve in response to detection of overpressure therein; and an integrated power supply (43) connected to said actuator and said pressure sensor, wherein said diaphragm has an unpowered position that closes said drainage conduit, and said sensor responds to the pressure inside said ocular cavity to electrically cause said diaphragm to move to a position that opens said drainage conduit, wherein each of said pressure sensor and said actuator diaphragm comprises a composite structure including a membrane (27) made of a biocompatible polymeric material having an inner face and an electro active polymer layer (29) sandwiched between two electrodes (31), a corresponding one of said electrodes affixed to an inner face of the membrane (27), wherein said drainage conduit includes tapered walls (37) adjacent the actuator at both the inlet and the outlet ends and converging in a drainage direction extending from said inlet end towards said outlet end to avoid reflux and facilitate passage of particles to avoid clogging during a pumping action, wherein said pressure sensor is connected to a generator for generating an electric field about said electrically-deformable diaphragm, and said pressure sensor is connected to said generator by a microprocessor (25), wherein said generator generates the electric field deforming said actuator diaphragm when said pressure sensor detects fluid pressure inside said drainage conduit exceeding a glaucoma threshold, and wherein said microapparatus is housed and integrated inside a capsule having a maximum dimension not greater than 3 mm.

2. The microapparatus according to claim 1, wherein said power supply comprises a passive receiver circuit adapted for coupling to an external power supply.

3. The microapparatus according to claim 2, wherein said circuit comprises an inductive wireless coupling (41-45).

4. The microapparatus according to claim 2, wherein said circuit comprises an integrated internal antenna adapted for coupling with an external antenna (41) connected to said external power supply (45).

5. The microapparatus according to claim 4, wherein said external antenna comprises an accessory affixed to the frame (49) or arm (47) of an eyeglass.

6. The microapparatus according to claim 1, wherein said power supply comprises an internal battery (43).

7. The microapparatus according to claim 6, wherein said battery comprises a rechargeable battery adapted for coupling by a recharging circuit to an external power supply.

8. The microapparatus according to claim 7, wherein said recharging circuit comprises an inductive wireless coupling (41-45).

9. The microapparatus according to claim 1, wherein said biocompatible polymeric material of the actuator diaphragm is selected from a group consisting of dielectric and nanocompound materials.

10. The microapparatus according to claim 1, wherein said pressure sensor comprises a piezoresistive membrane of biocompatible conductive polymeric material adapted to deform in response to pressure to thereby vary an electric resistance thereof.

11. The microapparatus according to claim 1, wherein said capsule is made of a material inhibiting fibrosis.

12. The microapparatus according to claim 11, wherein said capsule material inhibiting fibrosis includes parylene-C.

13. The microapparatus according to claim 1, wherein the inlet end of said drainage conduit is adapted for insertion into a sclera of the ocular cavity, a few millimeters behind a corneal limb, and the pressure sensor and the actuator are adapted for placement under the conjunctiva of the ocular cavity.

14. The microapparatus according to claim 1, wherein said polymeric material includes doped polypyrrole or other conjugated polymer.

* * * * *